US012593966B2

(12) United States Patent (10) Patent No.: US 12,593,966 B2
Yee et al. (45) Date of Patent: Apr. 7, 2026

(54) ENDOLUMINAL TRANSHEPATIC ACCESS PROCEDURE

(71) Applicant: Olympus Corporation, Tokyo (JP)

(72) Inventors: Gloria Yee, Westborough, MA (US);
Kunihide Kaji, Hachioji (JP)

(73) Assignee: Olympus Corporation, Tokyo (JP)

( * ) Notice: Subject to any disclaimer, the term of this patent is extended or adjusted under 35 U.S.C. 154(b) by 551 days.

(21) Appl. No.: 18/047,526

(22) Filed: Oct. 18, 2022

(65) Prior Publication Data

US 2023/0119097 A1 Apr. 20, 2023

Related U.S. Application Data

(60) Provisional application No. 63/263,720, filed on Nov. 8, 2021, provisional application No. 63/262,790, filed on Oct. 20, 2021.

(51) Int. Cl.
*A61B 1/00* (2006.01)
*A61B 1/018* (2006.01)
*A61B 17/00* (2006.01)

(52) U.S. Cl.
CPC .......... *A61B 1/018* (2013.01); *A61B 1/00087* (2013.01); *A61B 1/00154* (2013.01); *A61B 1/00066* (2013.01); *A61B 2017/003* (2013.01)

(58) Field of Classification Search
CPC . A61B 1/018; A61B 1/00087; A61B 1/00154; A61B 1/00066; A61B 1/000096
See application file for complete search history.

(56) References Cited

U.S. PATENT DOCUMENTS

| | | | |
|---|---|---|---|
| 10,902,944 B1* | 1/2021 | Casey .................... | A61B 34/25 |
| 2017/0014116 A1* | 1/2017 | Nakazato ................. | A61B 8/12 |
| 2019/0006047 A1* | 1/2019 | Gorek ..................... | G06F 18/25 |
| 2019/0125459 A1* | 5/2019 | Shelton, IV .......... | G16H 40/63 |
| 2019/0272917 A1* | 9/2019 | Couture ................. | G06N 20/00 |
| 2020/0029865 A1* | 1/2020 | Koike .................... | A61B 5/125 |
| 2020/0237452 A1* | 7/2020 | Wolf ....................... | G06F 3/048 |

(Continued)

OTHER PUBLICATIONS

Ogura et al. (Technical tips for endoscopic ultrasound-guided hepaticgastrostomy, World Journal of Gastroenterology, 22(15), 3945-3951 (Year: 2016).*

(Continued)

*Primary Examiner* — Timothy J Neal
(74) *Attorney, Agent, or Firm* — Schwegman Lundberg & Woessner, P.A.

(57) ABSTRACT

Systems, devices, and methods for providing an endoluminal transhepatic access to a patient pancreaticobiliary system in an endoscopic procedure are disclosed. An example of a transhepatic access procedure comprises navigating a steerable elongate instrument through a body cavity or channel and exiting to a access site of liver, puncturing the liver from the access site, extending the steerable elongate instrument through the liver and into the pancreaticobiliary system and performing an operation therein. Following the operation, the steerable elongate instrument can be retreated, and the access site of liver can be closed with a closure means. Apparatus and methods of training a machine-learning model and using said model to identify patient candidacy for retrograde access based on images of patient anatomy are also disclosed.

16 Claims, 9 Drawing Sheets

(56) References Cited

U.S. PATENT DOCUMENTS

| | | | |
|---|---|---|---|
| 2021/0169576 A1* | 6/2021 | Yoshinaka | G06N 20/00 |
| 2021/0228146 A1* | 7/2021 | Batchelor | A61B 1/00097 |

OTHER PUBLICATIONS

Nakal et al. (Endoscopic Ultrasound-Guided Biliary Drainage for Benign Biliary Diseases, Clinical Endoscopy, 52, 212-219 (Year: 2019).*

Mishra et al. (Endoscopic ultrasound guided biliary drainage: a comprehensive review, Translational Gastroenterology and Hepatology, 4:10 (Year: 2019).*

"Bayles Medical RF Transseptal Needle (video)", [Online]. Retrieved from the Internet: <URL: https://www.youtube.com/watch?v=rvKYIGWro74>, (Nov. 26, 2012), 1 pg.

"Baylis SupraCross RF Solution", [Online]. Retrieved from the Internet: <URL: https://www.baylismedical.com/system/resource_files/PRM-00101%20EN%20SupraCross%20Brochure%20Digital%20Spreads%20J-1,2,3%20V-3.pdf>, (Acessed Sep. 27, 2021), 3 pgs.

"Transhepatic Solution—Left Atrial Access from Any Approach", Baylis Medical, [Online]. Retrieved from the Internet: <URL: https://www.baylismedical.com/products/supracross-rf-solutions/transhepatic-solution/>, (Accessed Sep. 27, 2021), 6 pgs.

"VersaCross RF Transseptal Solution", [Online]. Retrieved from the Internet: <URL: https://www.baylismedical.com/ca/products/versacross-transseptal-platform/versacross-rf-transseptal-solution/>, (Accessed Sep. 27, 2021), 6 pgs.

Nguyen, Duy Thai, et al., "Percutaneous transhepatic access for catheter ablation of cardiac arrhythmias", Europace 15, (2013), 494-500.

Singh, Sheldon, et al., "Percutaneous Transhepatic Venous Access for Catheter Ablation Procedures in Patients With Interruption of the Inferior Vena Cava", Circulation: Arrhythmia and Electrophysiology, vol. 4, Issue 2, (2011), 235-241.

* cited by examiner

700

710

NAVIGATE A STEERABLE CATHETER THROUGH A BODY CAVITY OR CHANNEL AND EXIT TO A LIVER ACCESS SITE

720

PUNCTURE THE LIVER FROM THE ACCESS SITE

730

EXTEND THE STEERABLE CATHETER THROUGH THE LIVER AND INTO PANCREATICOBILIARY SYSTEM, AND PERFORM A DIAGNOSTIC OR THERAPEUTIC OPERATION

740

RETREAT THE STEERABLE CATHETER AND CLOSE THE LIVER ACCESS SITE AND LIVER TUNNEL

1

ENDOLUMINAL TRANSHEPATIC ACCESS PROCEDURE

CROSS REFERENCE TO RELATED APPLICATIONS

This application is related to commonly assigned U.S. Provisional Patent Application Ser. No. 63/262,790, entitled "ENDOLUMINAL TRANSHEPATIC ACCESS PROCEDURE", filed on Oct. 20, 2021 and U.S. Provisional Patent Application Ser. No. 63/263,720, entitled "ENDOLUMINAL TRANSHEPATIC ACCESS PROCEDURE", filed on Nov. 8, 2021, which are incorporated by reference in their entirety.

FIELD OF THE DISCLOSURE

The present document relates generally to endoscopic systems, and more particularly to systems and methods for performing an endoscopic procedure with endoluminal transhepatic access to a patient pancreaticobiliary system.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

In endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct Per-Oral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

Conventional ERCP and DPOC procedures use a retrograde approach to access a patient pancreaticobiliary system via duodenal papilla. Such retrograde access, however, may not be suitable for some patients due to restrictions such as their special or surgically altered anatomies. Automatic and computer-assisted identification of patient candidacy for retrograde access, and alternative endoscopic access route to pancreaticobiliary system for the non-candidates are generally desired.

SUMMARY

The present disclosure recognizes several technological problems to be solved with endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

Another challenge in conventional endoscopy is a high degree of variability of patient anatomy, especially patients with surgically altered or otherwise difficult anatomy. For example, in ERCP procedures, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. In another example, some patients have alternated papilla anatomy. With the duodenoscope designed to be stable in the duodenum, it can be more difficult to reach the duodenal papilla in surgically altered anatomy. Some endoscopic systems generally lack the capability of providing cannulation and endoscope navigation guidance based on patient's unique anatomy.

Conventional ERCP procedures have a failure rate of approximately 10-15%. Those patients are then usually referred for percutaneous transhepatic biliary drainage (PTBD) or surgical interventions. Some of the failed cases are related to surgically altered or otherwise difficult patient anatomy. For example, some patients may not be suitable for retrograde procedure (like conventional ERCP) to access the pancreaticobiliary system via duodenal papilla due to the unique or surgically altered anatomy. However, some endoscopic systems generally lack the capability of automatically identifying patient candidacy for retrograde access. The present inventors have recognized an unmet need for a computer-assisted identification of patient candidacy for retrograde procedure (e.g., conventional ERCP), and for those non-candidates, devices and techniques to facilitate alternative access route to the pancreaticobiliary system.

The present disclosure can help solve these and other problems by providing systems, devices, and methods for performing an endoscopic procedure with endoluminal transhepatic access to a patient pancreaticobiliary system, such as the bile duct. The transhepatic access procedure discussed in this document is an alternative to the retrograde access approach as used in conventional ERCP procedures. According to one aspect of the present disclosure, the transhepatic access procedure comprises steps of navigating a steerable elongate instrument through a body cavity or channel and exiting to a access site of liver, puncturing the liver from the access site via a working head of the steerable elongate instrument, extending the steerable elongate instrument through the liver and into the pancreaticobiliary system and performing a diagnostic or therapeutic procedure therein. The example transhepatic access procedure may further include retreating the steerable elongate instrument after the diagnostic or therapeutic operation, and closing the access site of liver using a closure means or member.

According to an aspect of the present disclosure, an artificial intelligence (AI)-based decision system can be used to select an appropriate endoscopic device and determine an appropriate endoscopic access approach, such as between the retrograde access and the antegrade transhepatic access, based on patient anatomy. A machine-learning (ML) model can be trained to determine patient candidacy for retrograde access approach based on, for example, an endoscopic image of duodenal papilla. For non-candidates, a transhepatic access procedure can be recommended to the operating physician, and a cannulation or endoscope navigation plan can be generated accordingly.

The endoluminal transhepatic procedure as described in this disclosure provides an alternative, antegrade approach to access the pancreaticobiliary system, which can be suitable for patients identified as non-candidates for conventional retrograde access, such as patients with unique or surgically altered anatomy that makes direct duodenal papilla access either impossible or infeasible. The AI-based patient candidacy identification as described herein can help avoid or reduce risks and complications associated with direct access via duodenal papilla in the non-candidate patients. Additionally, by identifying and excluding non-candidate patients from the conventional ERCP patient pool, the overall ERCP procedure success rate can be improved, and the healthcare cost associated with complications and procedure failures can be reduced.

Example 1 is a method for transhepatic access to a pancreaticobiliary system of a patient. The method comprises steps of: navigating a steerable elongate instrument through a body cavity or channel and exiting to an access site of liver; puncturing the liver from the access site using a working head of the steerable elongate instrument; and extending the steerable elongate instrument through the liver and into the pancreaticobiliary system, and performing a diagnostic or therapeutic operation therein.

In Example 2, the subject matter of Example 1 optionally includes navigating the steerable elongate instrument that can include exiting a wall of the duodenum and reaching the liver access site, wherein the body cavity or channel includes at least a portion of gastrointestinal (GI) tract including duodenum of small intestine.

In Example 3, the subject matter of Example 2 optionally includes navigating the steerable elongate instrument that can include passing the steerable elongate instrument through patient mouth.

In Example 4, the subject matter of any one or more of Examples 1-3 optionally includes puncturing the liver by applying mechanical force via a needle or a wire at the working head of the steerable elongate instrument.

In Example 5, the subject matter of any one or more of Examples 1-4 optionally includes puncturing the liver by applying radio-frequency (RF) energy to the access site of liver via the working head of the steerable elongate instrument.

In Example 6, the subject matter of any one or more of Examples 1-5 optionally includes the diagnostic or therapeutic operation that can include an endoscopic cholangiopancreatography (ERCP) procedure or a direct peroral cholangioscopy (DPOC) procedure.

In Example 7, the subject matter of any one or more of Examples 1-6 optionally includes the diagnostic or therapeutic operation that can include endoscopic tissue correction or biological matter retrieval.

In Example 8, the subject matter of any one or more of Examples 1-7 optionally includes, at the conclusion of diagnostic or therapeutic operation, retreating the steerable elongate instrument, and releasing from the steerable elongate instrument a closure means to close the access site of liver.

In Example 9, the subject matter of Example 8 optionally includes releasing the closure means by applying at least one of a biocompatible adhesive, a liquid-absorbable and expandable sponge, or a bioabsorbable plug to the access site.

In Example 10, the subject matter of any one or more of Examples 8-9 optionally includes releasing the closure means by deploying a stent into the access site.

In Example 11, the subject matter of any one or more of Examples 1-10 optionally includes identifying patient candidacy for transhepatic access to the pancreaticobiliary system based at least on an endoscopic image of duodenal papilla.

In Example 12, the subject matter of Example 11 optionally includes identifying the patient candidacy that can include applying the endoscopic image of duodenal papilla to a trained machine-learning (ML) model, the trained ML model being trained to establish a relationship between endoscopic images of duodenal papilla and pancreaticobiliary access approaches, and providing a recommendation of pancreaticobiliary access approach between (i) an retrograde access via duodenal papilla and (ii) the transhepatic access to the pancreaticobiliary system.

In Example 13, the subject matter of Example 12 optionally includes training the ML model using a training dataset comprising stored pancreaticobiliary access data from past endoluminal procedures on a plurality of patients, the stored pancreaticobiliary access data including (i) images of duodenal papilla of the plurality of patients and (ii) corresponding pancreaticobiliary access approaches.

Example 14 is an endoscopic system, comprising: a steerable elongate instrument configured for transhepatic access to a pancreaticobiliary system of a patient; a controller configured to: receive patient information including an image of duodenal papilla; and apply the received image of duodenal papilla to a trained machine-learning (ML) model to determine a pancreaticobiliary access approach between (i) an retrograde access via duodenal papilla and (ii) a transhepatic access to the pancreaticobiliary system; and an output unit configured to provide the determination of the pancreaticobiliary access approach to a user.

In Example 15, the subject matter of Example 14 optionally includes the controller that can be further configured to: construct a training dataset comprising stored pancreaticobiliary access data from past endoluminal procedures on a plurality of patients, the stored pancreaticobiliary access data including (i) images of duodenal papilla of the plurality of patient and (ii) corresponding pancreaticobiliary access approaches; and train the ML model using the training dataset.

In Example 16, the subject matter of any one or more of Examples 14-15 optionally includes the steerable elongate instrument that can include a catheter, a guide wire, or a guide sheath including a lumen to pass an elongated instrument therethrough.

In Example 17, the subject matter of any one or more of Examples 14-16 optionally includes the steerable elongate instrument that can include an endoscope, the endoscope including an imaging sensor to generate the image of duodenal papilla.

In Example 18, the subject matter of any one or more of Examples 14-17 optionally includes the steerable elongate instrument that can include a distal portion configured to navigate through a body cavity or channel, exit to an access site of liver, puncture the liver from the access site via a working head of the steerable elongate instrument, and pass through the liver and into the patient pancreaticobiliary system.

In Example 19, the subject matter of Example 18 optionally includes the steerable elongate instrument that can be configured to puncture the access site of liver via a mechanical force or radio-frequency energy applied to the working head.

In Example 20, the subject matter of any one or more of Examples 18-19 optionally includes the steerable elongate instrument that can be configured to deploy a closure means to the access site of liver at the conclusion of a diagnostic or therapeutic operation at the pancreaticobiliary system.

In Example 21, the subject matter of Example 20 optionally includes the closure means including at least one of a biocompatible adhesive, a liquid-absorbable and expandable sponge, or a bioabsorbable plug.

In Example 22, the subject matter of any one or more of Examples 20-21 optionally includes the closure means including a stent.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

This document describes systems, devices, and methods for providing an endoluminal transhepatic access to a patient pancreaticobiliary system in an endoscopic procedure. According to an example, a transhepatic access procedure comprises navigating a steerable elongate instrument through a body cavity or channel and exiting to a access site of liver, puncturing the liver from the access site, extending the steerable elongate instrument through the liver and into the pancreaticobiliary system and performing an operation therein. Following the operation, the steerable elongate instrument can be retreated, and the access site of liver can be closed with a closure means. According to some examples, an AI-based access decision system can be used to identify patient candidacy for the conventional retrograde access approach, such as based on patient anatomy of interest. For non-candidates, a transhepatic access procedure as described in this disclosure can be recommended.

Figure 1:
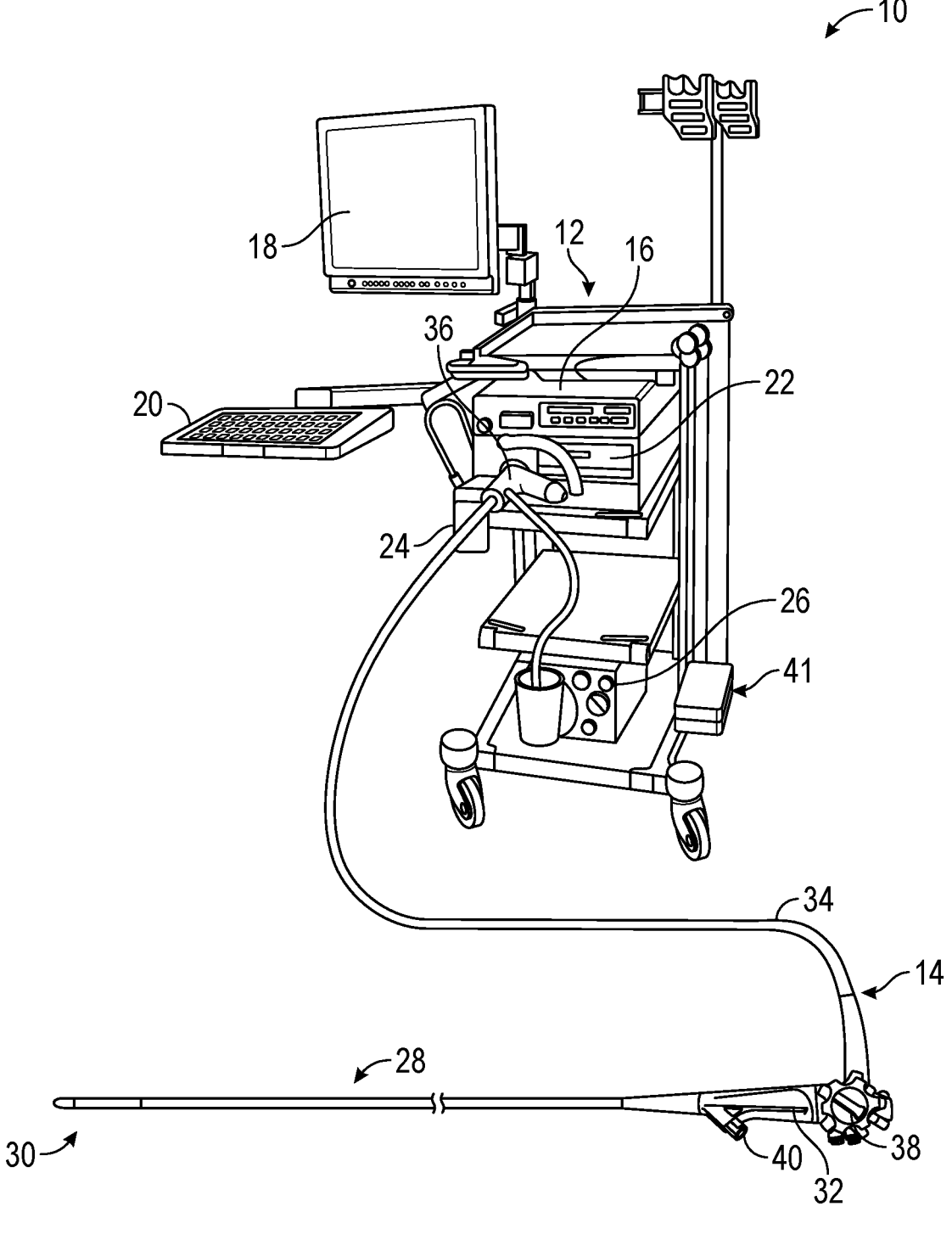
FIGS. 1-2 are schematic diagrams illustrating an example of an endoscopy system for use in endoscopic procedures such as an ERCP procedure.

FIG. 1 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 can include various ports for coupling with endoscopy system 10. For example, the control unit 16 can include a data input/output port for receiving data from and communicating data to the endoscope 14. The light source 22 can include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by an operator of endoscopy system 10 to control functions of endoscopy system 10 and view output of endoscope 14. In some examples, the control unit 16 can additionally be used to generate signals or other outputs for treating the anatomical region into which the endoscope 14 is inserted. Examples of such signals or outputs can include electrical output, acoustic output, a radio-frequency energy output, a fluid output and the like for treating the anatomical region with, for example, cauterizing, cutting, freezing and the like.

The endoscope 14 can interface with and connect to imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

Figure 4:
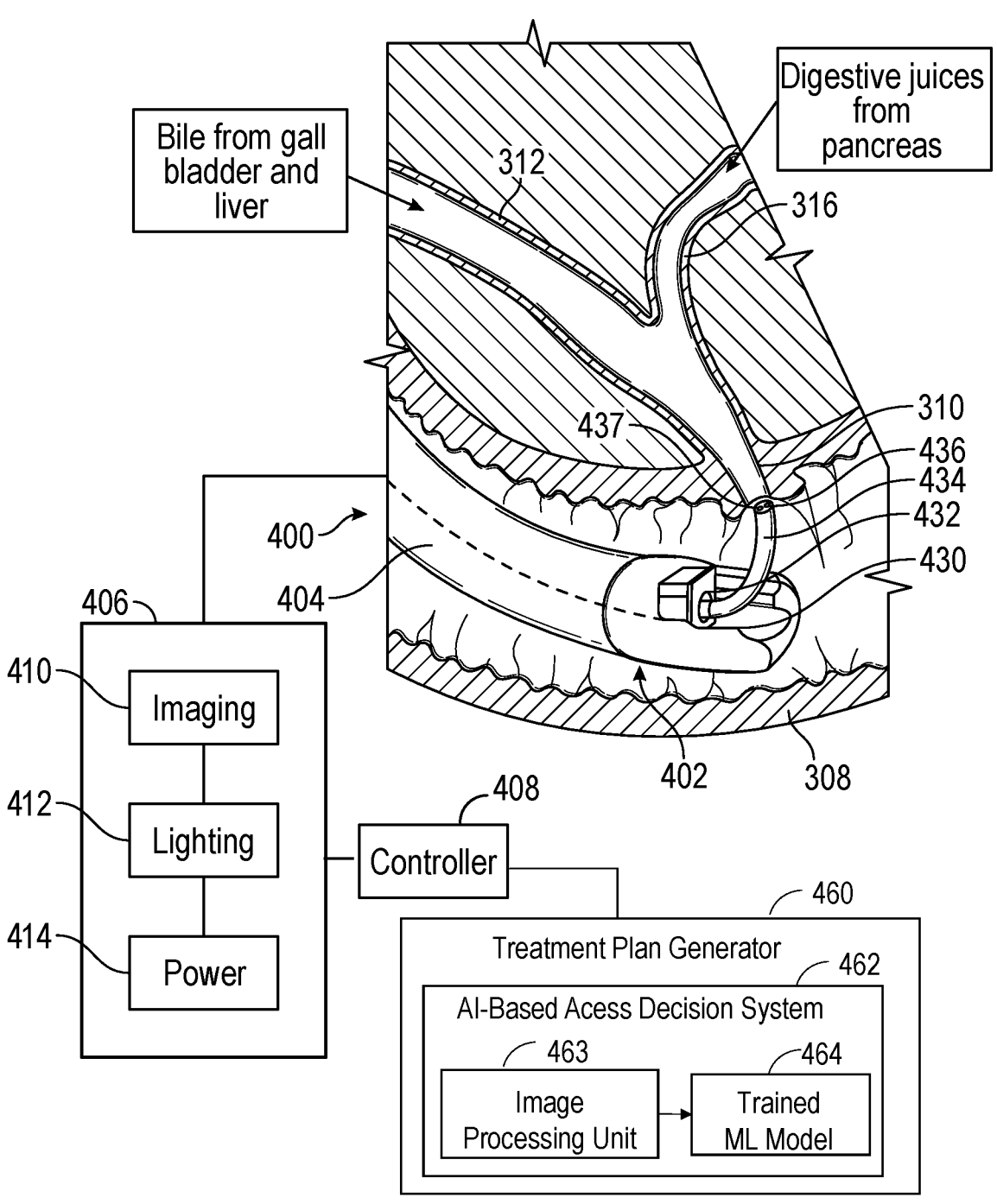
FIG. 4 is a diagram illustrating an example of mother-daughter endoscopes used in an ERCP procedure, and a portion of patient anatomy where the procedure is performed.

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope as shown in FIG. 4. The working channel can extend between handle section 32 and functional section 30. Additional functionalities, such as fluid passages, guidewires, and pull wires can also be provided by insertion section 28 (e.g., via suction or irrigation passageways, and the like).

The handle section 32 can comprise a control knob 38 and ports 40. The ports 40 can be configured to couple various electrical cables, guidewires, auxiliary scopes, tissue collection devices of the present disclosure, fluid tubes and the like to handle section 32 for coupling with insertion section 28.

The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 2) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 2), etc. Alternatively, several components of the imaging and control system 12 shown in FIGS. 1 and 2 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

Figure 2:
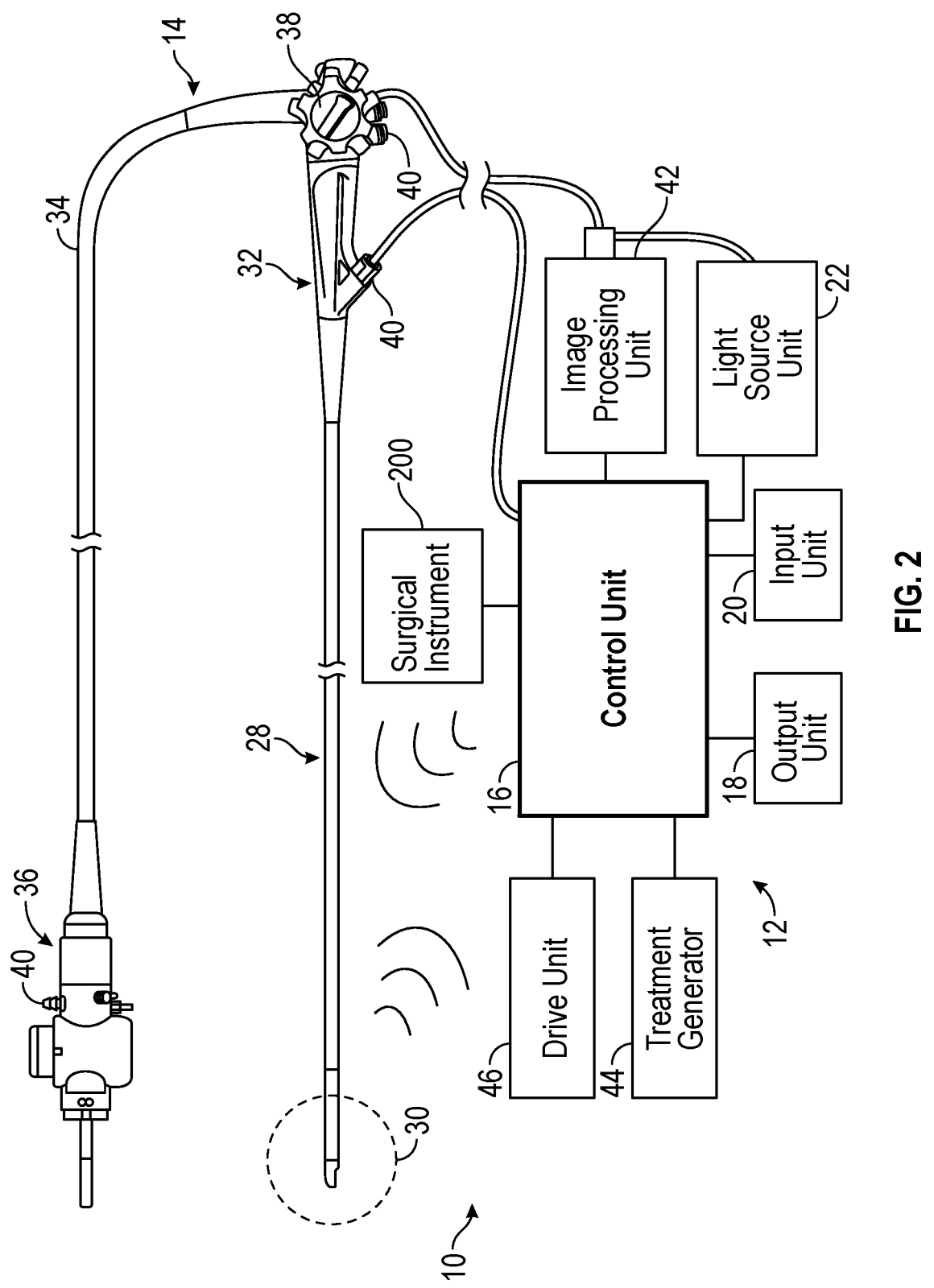

FIG. 2 is a schematic diagram of the endoscopy system 10 shown in FIG. 1, which comprises the imaging and control system 12 and the endoscope 14. FIG. 2 schematically illustrates components of the imaging and control system 12 coupled to the endoscope 14, which in the illustrated example comprises a duodenoscope. The imaging and control system 12 can comprise a control unit 16, which can include or be coupled to an image processing unit 42, a treatment generator 44, and a drive unit 46, as well as the light source 22, the input unit 20, and the output unit 18 as discussed above with reference to FIG. 1. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which can include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 can include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

The treatment generator 44 can generate a treatment plan, which can be used by the control unit 16 to control the operation of the endoscope 14, or to provide with the operating physician a guidance for maneuvering the endoscope 14, during an endoscopic procedure. In an example, the treatment generator 44 can use a trained machine-learning (ML) model to determine patient candidacy for retrograde access to the pancreaticobiliary system via duodenal papilla, such as based on an endoscopic image of duodenal papilla. For non-candidates, the treatment generator 44 can recommend a transhepatic access procedure as an alternative to the conventional retrograde access. The treatment generator 44 can generate a cannulation or endoscope navigation plan in accordance with the determined access route (i.e., either retrograde access or transhepatic access). The endoscope navigation plan may include suggested values for one or more cannulation or navigation parameters. Examples of determining between retrograde access or transhepatic access for a patient and the procedures involved in the transhepatic access are discussed below with reference to FIGS. 4 and 5.

Figure 3A:
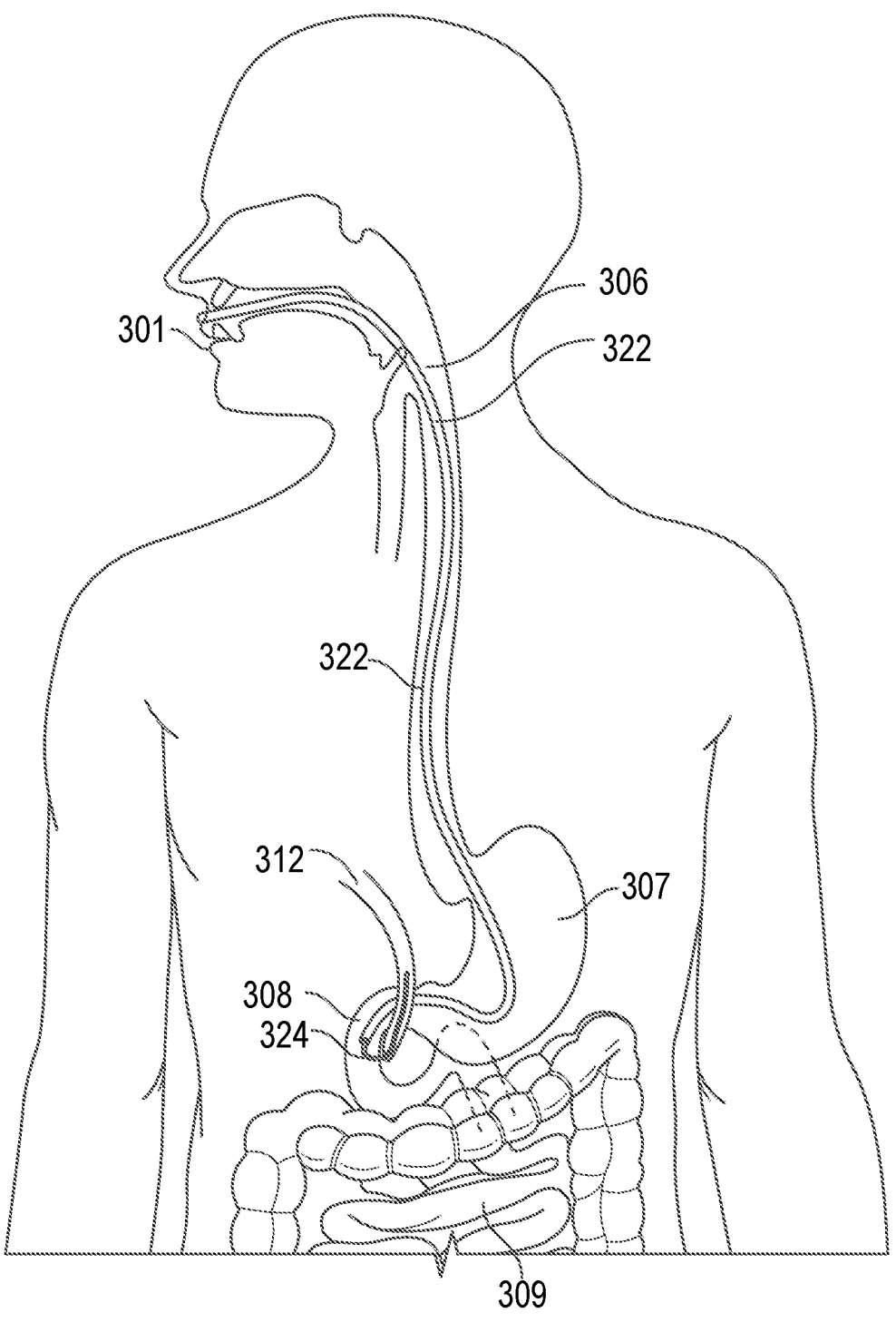
FIGS. 3A-3B are diagrams illustrating an example of peroral cholangioscopy involving direct insertion of a cholangioscope into patient bile duct as in a DPOC procedure, and a portion of patient anatomy where the procedure is performed.
Figure 3B:
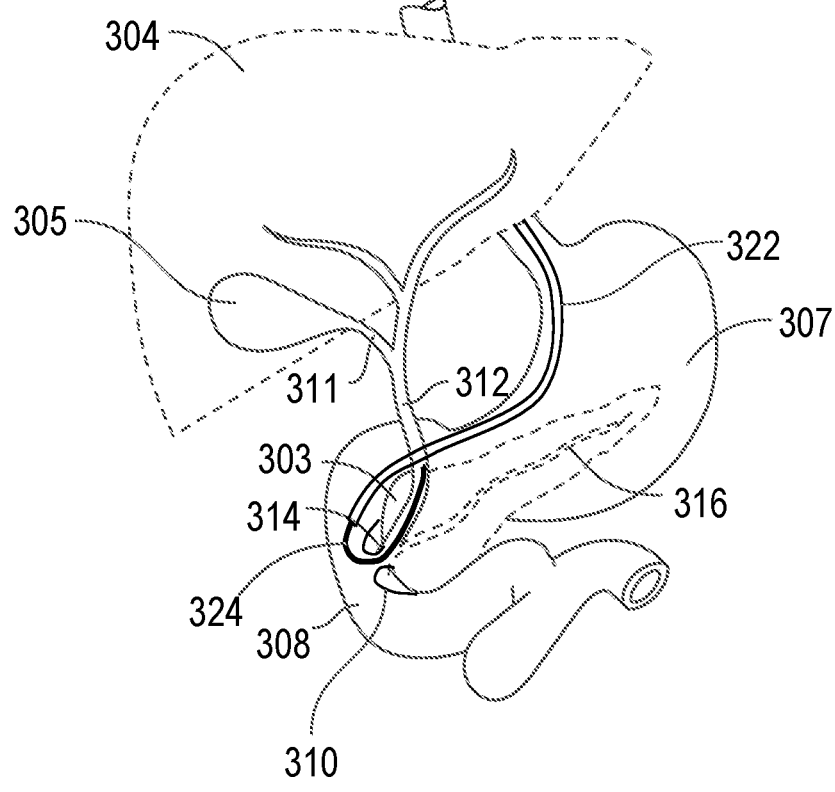

FIGS. 3A-3B are diagrams illustrating an example of peroral cholangioscopy performed via direct insertion of a cholangioscope 324 into the bile duct, as in a DPOC procedure, and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310 (FIG. 3B). The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

FIG. 3B is a schematic view of duodenum 308 connected to common bile duct 312 via duodenal papilla 314. Common bile duct 312 can branch off into pancreatic duct 316 and gallbladder duct 311. Duodenal papilla 314 can include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it may be desirable during medical procedures to cut sphincter of Oddi 310 to enlarge duodenal papilla 314 to allow for easier access of instrument into common bile duct 312.

FIG. 4 is a diagram illustrating an example of mother-daughter endoscopes used in an ERCP procedure, and a portion of patient anatomy where the procedure is performed. The mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 can include, or be coupled to, a controller 408. Similar to the discussion above with respect to FIG. 1, the control module 406 can include other components, such as those described with reference to endoscopy system 10 (FIG. 1) and control unit 16 (FIG. 2). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 1 and 2.

The functional module 402 of the main scope 400 can comprise an elevator portion 430. The auxiliary scope 434 can itself include functional components, such as camera lens 437 and a light lens (not illustrated) coupled to control module 406, to facilitate navigation of the auxiliary scope 434 from the main scope 400 through the anatomy and to facilitate viewing of components extending from lumen 432.

In ERCP, the auxiliary scope 434 can be guided into the sphincter of Oddi 310. Therefrom, a surgeon operating the auxiliary scope 434 can navigate the auxiliary scope 434 through the lumen 432 of the main scope toward the gallbladder 305, liver 304, or other locations in the gastrointestinal system to perform various procedures. In some examples, the auxiliary scope 434 can be used to guide an additional device to the anatomy to obtain biological matter (e.g., tissue), such as by passage through or attachment to lumen 436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 400 and the auxiliary scope 434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 408 can include, or be coupled to, a treatment plan generator 460. The treatment plan generator 460, which is an example of the treatment generator 44 as illustrated in FIG. 2, can automatically generate a treatment plan, including an appropriate endoscopic device and an access approach to the pancreaticobiliary system in a peroral cholangioscopic procedure. As stated above, conventional peroral cholangioscopy (e.g., ERCP and DPOC) uses retrograde access approach involving passing an endoscope (or other elongate instrument such as a catheter or guidewire) from patient mouth and through the GI tract, exiting duodenum from duodenal papilla, and entering the bile duct. However, some patients may not be suitable for retrograde access due to, for example, surgically altered or otherwise difficult anatomy. The treatment plan generator 460 can include an AI-based access decision system 462 that can identify patient candidacy for retrograde access procedure, and generate an recommendation of either the conventional retrograde access approach or a transhepatic antegrade access approach as described in this disclosure. Examples of the transhepatic antegrade access approach are discussed below with reference to FIGS. 5A and 5B.

The AI-based access decision system 462 can identify patient candidacy for retrograde access approach, or determine between the retrograde access approach and the transhepatic antegrade access approach, based on patient anatomy of interest. Images (or video frames) of an anatomical target can be obtained from imaging studies, such as X-rays, fluoroscopy images, CT images, MRI images such as image obtained from Magnetic resonance cholangiopancreatography (MRCP), or endoscopic ultrasonography (EUS) images.

An example of the anatomical target is duodenal papilla and its surrounding environment. In an example, the AI-based access decision system 462 can use endoscopic images of duodenal papilla captured by the imaging device (e.g., a camera) of the endoscope to identify patient candidacy for retrograde access approach, or to recommend between the retrograde access approach and the transhepatic antegrade access approach. The AI-based access decision system 462 can include an image processing unit 463 and a trained machine-learning (ML) model 464. The image processing unit 463 can receive images of anatomy of interest, including endoscopic images of duodenal papilla and its surrounding environment acquired during a previous endoscopic procedure, and extract one or more geometric or morphological features from the image. The images or image features extracted therefrom can be applied to the trained ML model 464. The ML model 464 may be trained to establish a relationship between endoscopic images or image features of duodenal papilla and pancreaticobiliary access approaches (e.g., either the retrograde access approach, or the transhepatic antegrade access approach). In an example, information about the pancreaticobiliary access approaches can be stored in a database in a cloud and/or a local system. The AI-based access decision system 462 can access the database, retrieve therefrom the pancreaticobiliary access approaches information, and using such information to train the ML model.

The ML model 464 may be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN), a deep belief network (DBN), or a hybrid neural network comprising two or more neural network models of different types or different model configurations. In an example, the training of a ML model may include constructing a training dataset using pancreaticobiliary access data collected from past procedures performed on a plurality of patients. The past pancreaticobiliary access data can be stored in a database accessible by the AI-based access decision system 462. The stored pancreaticobiliary access data can include images of duodenal papilla of the plurality of patient, the pancreaticobiliary access approaches used in the procure (either retrograde access or transhepatic antegrade access), cannulation and navigation parameters associated with the procedure (e.g., position, heading direction or angle, amount of protrusion, speed or force applied to the endoscope, or navigation path toward the anatomical target of interest, among others), and the outcome of the procedure (e.g., success rate and patient complications). The training of the ML model may be performed continuously or periodically, or in near real time as additional pancreaticobiliary access data are made available. The training involves algorithmically adjusting one or more ML model parameters, until the ML model being trained satisfies a specified training convergence criterion. The The trained ML model can be validated, and implemented in the AI-based access decision system 462. The AI-based access decision system 462 may apply the image of the patient anatomy, or the image features such as generated by the image processing unit 463, to the trained ML model 464 to determine patient candidacy for retrograde access, or to generate a recommendation of either the retrograde access approach or the transhepatic antegrade access approach. The trained ML model 464 may additionally be used to determine a treatment plan including cannulation and navigation parameters, and/or to predict a success rate for the procedure to be performed on the current patient. Commonly assigned U.S. Provisional Patent Application Ser. No. 63/263,720, entitled "ENDOLUMINAL TRANSHEPATIC ACCESS PROCEDURE", filed on Nov. 8, 2021, discusses ML models and using the same to generate a treatment plan, the disclosure of which is hereby incorporated by reference in its entirety.

Figures 5A, 5B:
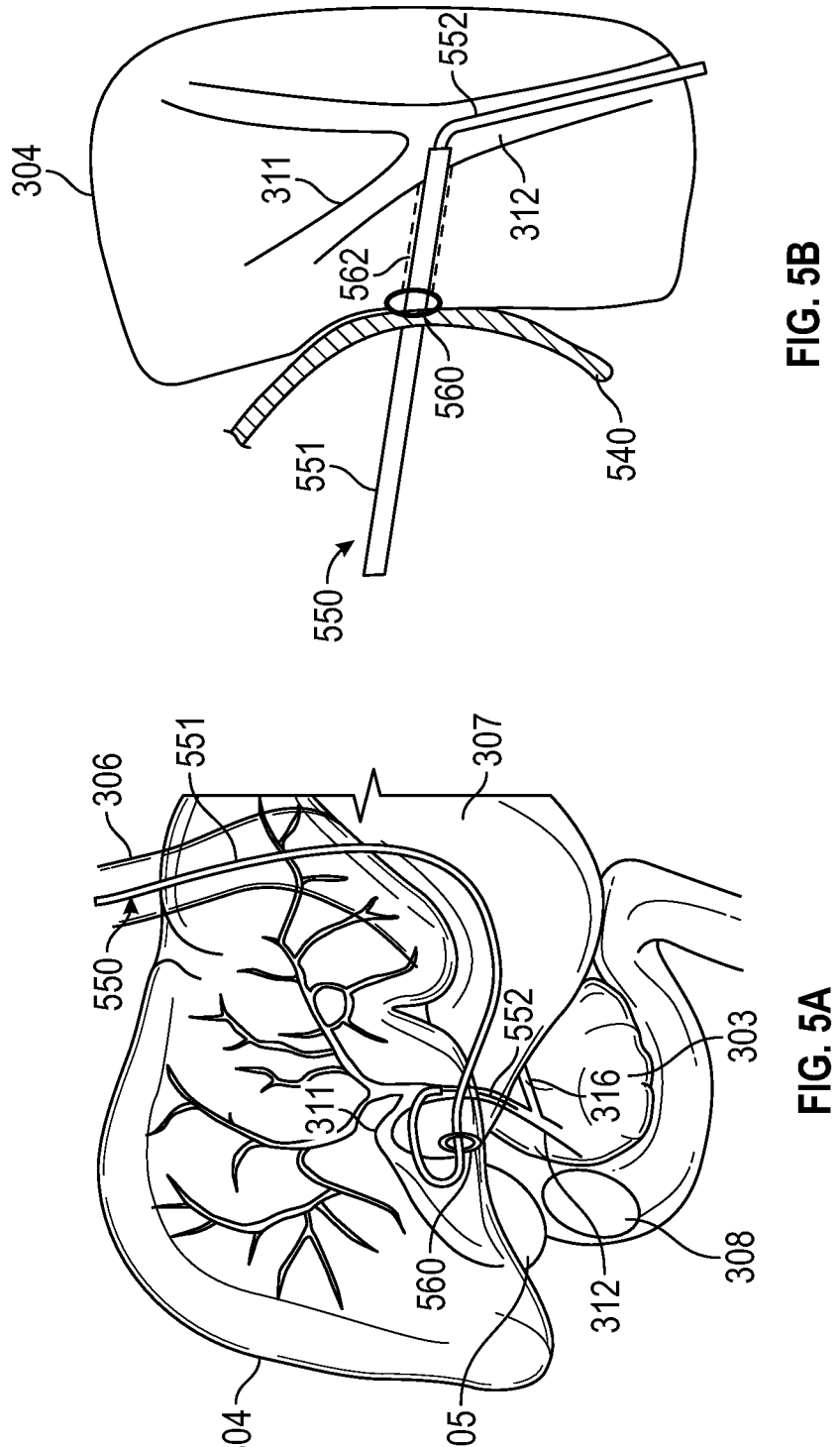
FIGS. 5A-5B are diagrams illustrating an example of the transhepatic approach to access the pancreaticobiliary system where the diagnostic or therapeutic operations can be performed.

FIGS. 5A-5B are diagrams illustrating an example of the transhepatic approach to access the pancreaticobiliary system (e.g., the common bile duct or the pancreatic duct) to perform diagnostic or therapeutic operations. The transhepatic approach is an alternative to the conventional retrograde approach (like in conventional ERCP or DPOC) of accessing patient pancreaticobiliary system. As stated above with reference to FIGS. 3A-3B and 4, the retrograde approach involves passing an endoscope or a catheter through mouth 301, esophagus 306, stomach 307, and a portion of duodenum 308, and then exiting to common bile duct 312 via duodenal papilla 314. In contrast, the transhepatic approach involves operably passing a steerable elongate instrument 550 (e.g., the elongate portion of an flexible endoscope, a guidewire, a catheter, or a guide sheath) through a body cavity or channel (e.g., a portion of the GI tract) and exiting to an access site of the liver 304. FIG. 5A illustrates by way of example the placement of steerable elongate instrument 550 and a portion of the anatomical environment. FIG. 5B is a schematic diagram illustrating the transhepatic steerable elongate instrument 550 entering the liver 304 from duodenum wall 540. As illustrated in FIGS. 5A-5B, the steerable elongate instrument 550 can be inserted into patient mouth, operably pass down the esophagus 306, the stomach 307, and a portion of small intestine such as duodenum 308. The steerable elongate instrument 550 can then exit from the duodenum wall 540 to an access site 560 of the liver 304.

A working head at a distal portion of the steerable elongate instrument 550 can puncture the liver 304 from the access site 560. The steerable elongate instrument 550 can advance through the liver 304, produce a liver tunnel 562, and enter into the pancreaticobiliary system, such as the gallbladder duct 311 or the common bile duct 312. The steerable elongate instrument 550 can perform diagnostic or therapeutic operation at target duct location, such as collecting and retrieving biological matter (e.g., tissue, gallstone)

via one or more biological matter collection and retrieval devices associated with the steerable elongate instrument 550, or surgically managing stricture or blockage.

In some examples, as illustrated in FIGS. 5A and 5B, the steerable elongate instrument 550 can include a first elongate device 551, and a second elongate device 552 nested inside the first elongate device 551, such as a lumen or a working channel of the first elongate device 551. At least a portion of the second elongate device 552 can slide or rotate inside the lumen or the working channel of the first elongate device 551 under the user control. In one example, the first elongate device 551 is a catheter or a guide sheath, and the second elongate device 552 is a guidewire or the cholangioscope 104. In another example, the first and second elongate devices can be mother-daughter endoscopes, where the first elongate device 551 is the main scope 400 (duodenoscope), and the second elongate device 552 is the auxiliary scope 434 (cholangioscope) at least partially nested within a lumen of the first elongate device 551. The first elongate device 551 can pass through the GI tract portion, puncture the duodenum wall 540 and the liver access site 560, and enter into the duct system (e.g., common bile duct 312). Then the second elongate device 552 can advance from a distal portion of the first elongate device 551, further navigate through different duct locations, and perform diagnostic or therapeutic operations. The second elongate device 552 may include one or more biological matter collection and retrieval devices that can collect and retrieve biological matter, or surgically managing stricture or blockage.

Mechanical force or energy of various sources may be applied to the working head to facilitate penetrating the duodenum wall 540, and puncturing and tunneling the liver from the access site 560. Mechanical force can be manually applied by the operating physician, or at least partially robotically applied. In an example, the working head of the steerable elongate instrument 550 can include a puncture member located at the distal portion of the steerable elongate instrument 550. Examples of the puncture member can include a needle, a wire, an auger, among others. In another example, the working head can include an emitter coupled to an energy source to emit energy to the duodenum wall and the liver at the access site to facilitate penetration and tunneling. Examples of the energy sources may include thermal energy, radio-frequency, ultrasound, or molecular resonance, among others.

Figures 6A, 6B, 6C, 6D:
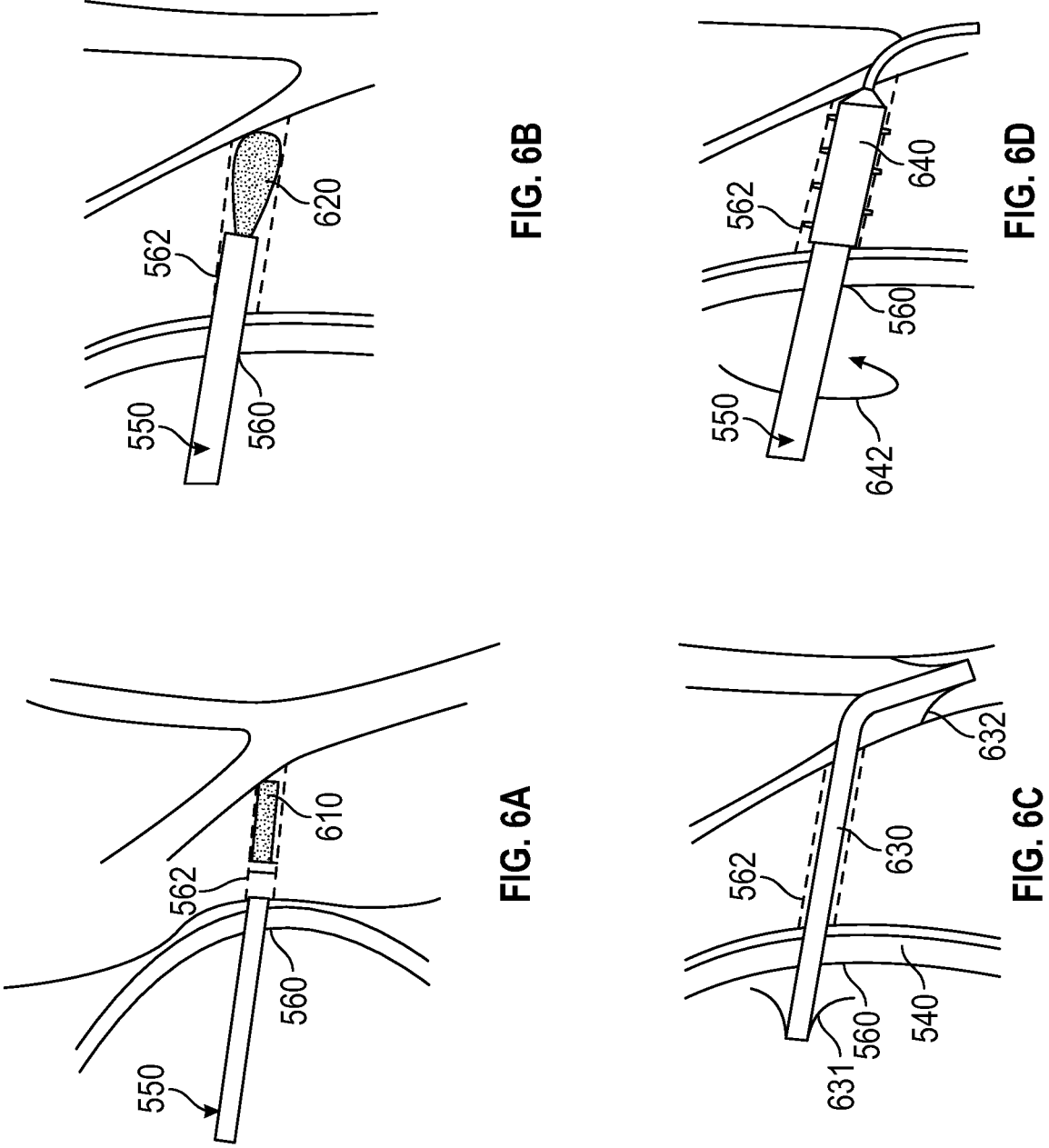
FIGS. 6A-6D illustrate example means for closing the access site and the tunnel of liver at the conclusion of an endoscopic procedure with endoluminal transhepatic access to the pancreaticobiliary system.

After the transhepatic procedure performed at the pancreaticobiliary duct system, the steerable elongate instrument 550 can be retreated, and the access site 560 and the liver tunnel 562 can be closed. FIGS. 6A-6D illustrate by way of example and not limitation various approaches for closing the access site 560 and the liver tunnel 562. FIG. 6A illustrates biocompatible adhesives 610 being applied to the access site 560 and filled into the liver tunnel 562. The adhesives 610 can be in gel form (e.g., fibrin adhesive) or power form (e.g., sodium alginate). FIG. 6B illustrates a liquid-absorbable and expandable sponge 620 (e.g., cellulose fiber) being filled into the access site 560 and the liver tunnel 562. In some examples, the adhesives 610 or the sponge 620 can be released from the steerable elongate instrument 550 as it withdraws from the access site 560 and the liver tunnel 562.

FIG. 6C illustrates a stent 630 being inserted into the access site 560 and the liver tunnel 562. The stent 630 can be expanded to securely fit into the tunnel 562. The stent 630 may include anchors or other locking mechanisms to enhance stability after being deployed. In the example shown in FIG. 6C, one anchor 631 at a distal end of the stent can be anchored to the duodenum wall 540, another anchor 632 at a proximal end of the stent can be anchored to the wall of common bile duct 312. In an example, the stent 630 may maintain a drainage function. The stent 630 may be released from the steerable elongate instrument 550 as it withdraws from the access site 560 and the liver tunnel 562.

FIG. 6D illustrates a plug 640 being inserted into the access site 560 and the liver tunnel 562. The plug 640 can be made of bioabsorbable material (e.g., polyglycolic acid) such that it can be absorbed by the living tissue. In the illustrated example, the plug 640 can be a screw plug being deployed at the access site 560 and affixed onto the liver tunnel 562, such as via a screw or other securing mechanism. The steerable elongate instrument 550 can engage with the plug 640. The operating physician can twist the steerable elongate instrument 550 in a direction 642 to advance the plug 640 into the liver tunnel 562. When the plug is deployed to a desired location, the steerable elongate instrument 550 can be disengaged from the plug 640 and withdrawn from the surgical site.

Figure 7:
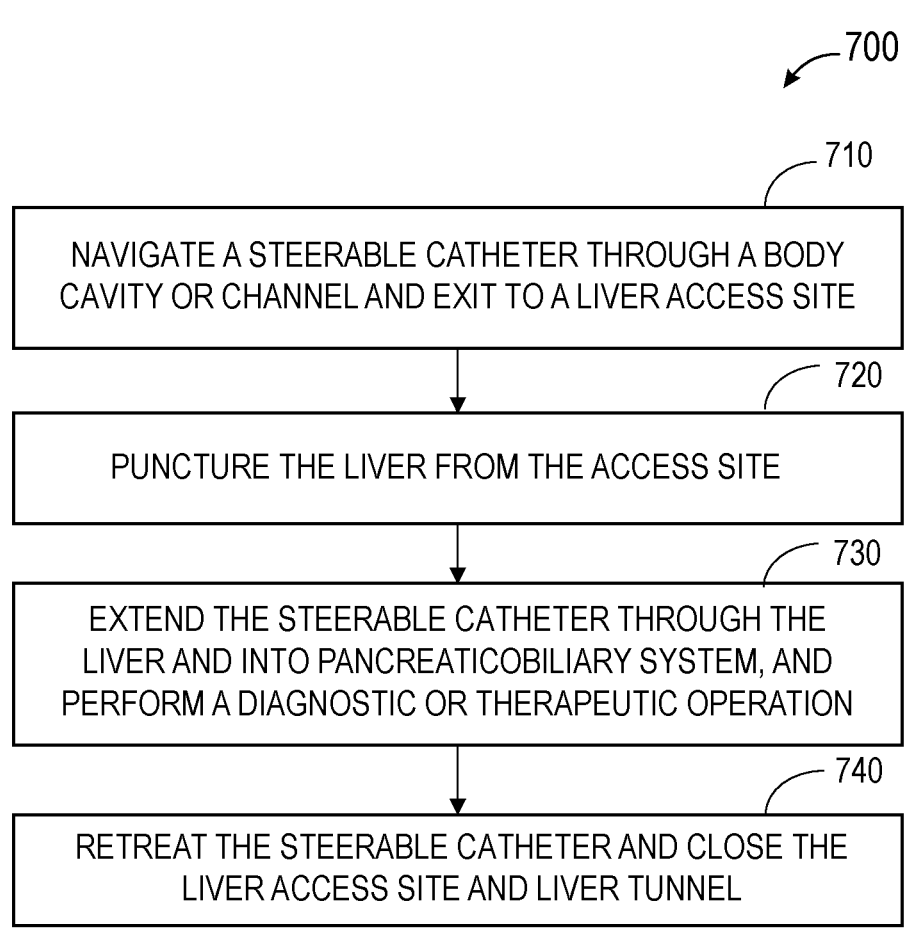
FIG. 7 is a flow chart illustrating an example method for transhepatic access to patient pancreaticobiliary system to perform diagnostic or therapeutic operations therein.

FIG. 7 is a flow chart illustrating an example method 700 for transhepatic access to patient pancreaticobiliary system to perform diagnostic or therapeutic operations therein. The transhepatic approach is an alternative to the conventional retrograde approach as used in conventional ERCP or DPOC procedures where the patient pancreaticobiliary system is endoluminally accessed via the duodenal papilla.

At 710, a steerable elongate instrument can be navigated through a body cavity or channel, such as portion of patient GI tract including the mouth, the esophagus, the stomach, and the duodenum, as illustrated in FIG. 5A. Examples of the steerable elongate instrument may include an elongate portion of an flexible endoscope, a guidewire, a catheter, or a guide sheath. The steerable elongate instrument can exit the duodenum wall and reach an access site of liver.

At 720, the liver can be punctured from the access site using a working head of the steerable elongate instrument. In an example, mechanical force may be applied manually or robotically to the working head, such as a needle, a wire, or an auger, to facilitate penetrating the duodenum wall, and puncturing and tunneling the liver. In another example, energy of various types (e.g., thermal energy, radio-frequency, ultrasound, or molecular resonance) may be applied to the duodenum wall and the liver at the access site to facilitate penetration and tunneling.

At 730, the steerable elongate instrument may advance through the liver and enter into the pancreaticobiliary system, such as the gallbladder duct or the common bile duct. The steerable elongate instrument can perform diagnostic or therapeutic operation at target duct location, such as collecting and retrieving biological matter (e.g., tissue, gallstone) via one or more biological matter collection and retrieval devices associated with the steerable elongate instrument, or surgically managing stricture or blockage.

At 740, at the conclusion of the transhepatic procedure performed at the pancreaticobiliary duct system, the steerable elongate instrument can be retreated, and the liver access site and the liver tunnel can be closed using a closure means. Examples of the closure means, as illustrated in FIGS. 6A-6D, can include a biocompatible adhesive, a liquid-absorbable and expandable sponge, a bioabsorbable plug, or a stent. In an example, the closure means can be released from the steerable elongate instrument as it retreats from the liver tunnel.

Figure 8:
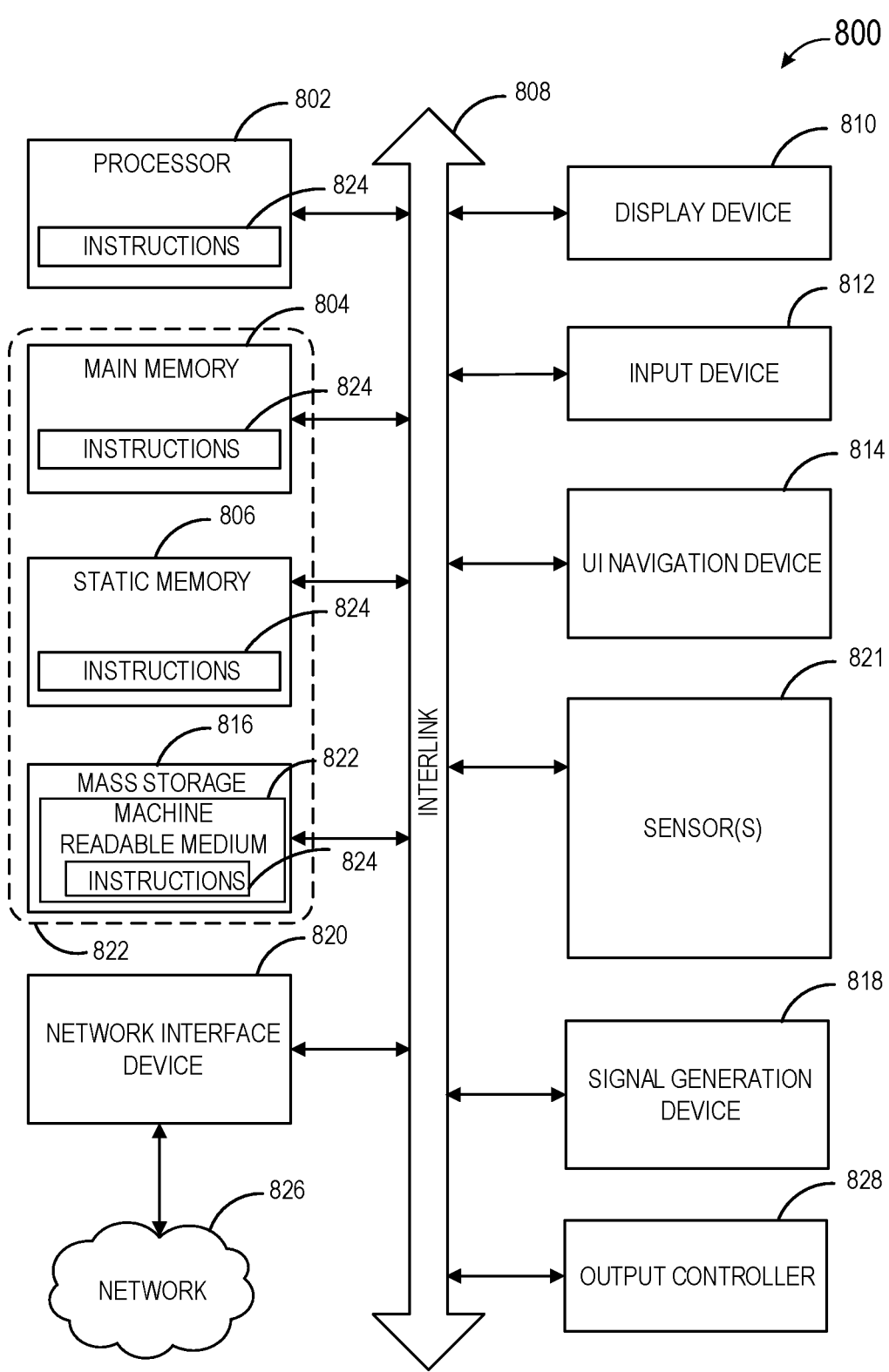
FIG. 8 is a block diagram illustrating an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the treatment plan generator 460, such as the AI-based access decision system 462.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device

812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 824 may further be transmitted or received over a communication network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communication network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An endoscopic system, comprising:
a steerable elongate instrument configured for transhepatic access to a pancreaticobiliary system of a patient;
a controller circuit configured to:
receive patient information including an image of a duodenal papilla;
apply the received image of the duodenal papilla to a trained machine-learning (ML) model to determine a pancreaticobiliary access approach between (i) a retrograde access via the duodenal papilla and (ii) a transhepatic access to the pancreaticobiliary system;
extract at least one of a geometric feature or a morphological feature from the image of the duodenal papilla; and
predict, using the trained machine-learning model and the extracted geometric feature or morphological feature, one or more anatomical complication outcomes for the determined pancreaticobiliary access approach; and
a display configured to provide a treatment plan including cannulation and navigation parameters for the steerable elongate instrument and the predicted one or more anatomical complication outcomes, based on the determination of the pancreaticobiliary access approach to a user.

2. The endoscopic system of claim 1, wherein the controller circuit is further configured to:
construct a training dataset comprising stored pancreaticobiliary access data from past endoluminal procedures on a plurality of patients, the stored pancreaticobiliary access data including (i) one or more images of the duodenal papilla of the plurality of patients and (ii) corresponding pancreaticobiliary access approaches; and
train the ML model using the training dataset.

3. The endoscopic system of claim 1, wherein the steerable elongate instrument includes a catheter, a guide wire, or a guide sheath including a lumen to pass an elongated instrument therethrough.

4. The endoscopic system of claim 1, wherein the steerable elongate instrument includes an endoscope, the endoscope including an imaging sensor to generate the image of duodenal papilla.

5. The endoscopic system of claim 1, wherein the steerable elongate instrument includes a distal portion configured to navigate through a body cavity or channel, exit to an access site of a liver, puncture the liver from the access site via a working head of the steerable elongate instrument, and pass through the liver and into the pancreaticobiliary system of the patient.

6. The endoscopic system of claim 5, wherein the steerable elongate instrument is configured to puncture the access site of the liver via a mechanical force or radio-frequency energy applied to the working head.

7. The endoscopic system of claim 5, wherein the steerable elongate instrument is further configured to deploy a closure member to the access site of the liver at a conclusion of a diagnostic or therapeutic operation at the pancreaticobiliary system.

8. The endoscopic system of claim 1, wherein the image of a duodenal papilla includes at least one of an X-ray image, a fluoroscopy image, or a CT image.

9. The endoscopic system of claim 1, wherein the image of a duodenal papilla includes at least one of a Magnetic Resonance CholangioPancreatography (MRCP) image or an Endoscopic UltraSonography (EUS) image.

10. The endoscopic system of claim 1, further comprising the trained machine-learning (ML) model, wherein the ML model has been trained using a training dataset using pancreaticobiliary access data.

11. The endoscopic system of claim 10, wherein the pancreaticobiliary access data includes at least one of:

past pancreaticobiliary access approaches;

past cannulation and navigation parameters; or success rate and patient complications.

12. The endoscopic system of claim 10, wherein the cannulation and navigation parameters include at least one of:

position of the steerable elongate instrument;

heading direction or angle of the steerable elongate instrument;

amount of protrusion of the steerable elongate instrument;

speed or force applied to the steerable elongate instrument; or navigation path toward an anatomical target of interest.

13. The endoscopic system of claim 1, wherein the one or more anatomical complication outcomes include one or more complications associated with one or more of surgically altered anatomy, a compressed duodenum, or altered papilla anatomy that would affect a transhepatic access procedure.

14. The endoscopic system of claim 1, wherein training the ML model includes adjusting one or more model parameters until the ML model satisfies a training convergence criterion.

15. The endoscopic system of claim 1, wherein the controller circuit is further configured to:

extract the at least one of a geometric or morphological feature from an image of a surrounding environment of the duodenal papilla.

16. The endoscopic system of claim 15, further comprising:

an image processing unit separate from the trained machine-learning model, wherein the controller circuit uses the image processing unit to extract the at least one of a geometric or a morphological feature from the image of the duodenal papilla or the image of the surrounding environment of the duodenal papilla before applying the image to the trained machine-learning model.

* * * * *